United States Patent [19]

Klein et al.

[11] Patent Number: 4,973,759

[45] Date of Patent: Nov. 27, 1990

[54] PROCESS FOR THE ISOLATION OF ALKYLATED AROMATIC AMINES

[75] Inventors: Alfons Klein, Duesseldorf; Helmut Fiege, Leverkusen, both of Fed. Rep. of Germany

[73] Assignee: Bayer Aktiengesellschaft, Leverkusen, Fed. Rep. of Germany

[21] Appl. No.: 410,183

[22] Filed: Sep. 20, 1989

[30] Foreign Application Priority Data

Oct. 7, 1988 [DE] Fed. Rep. of Germany ....... 3834196

[51] Int. Cl.$^5$ .................... C07C 45/00; C07C 45/90
[52] U.S. Cl. .................... 564/437; 564/305; 564/409; 564/433
[58] Field of Search ............ 564/437, 305, 307, 409, 564/433, 434, 442

[56] References Cited

U.S. PATENT DOCUMENTS

| | | | |
|---|---|---|---|
| 2,187,820 | 8/1938 | Lecher et al. | 564/437 |
| 2,814,646 | 11/1957 | Kolka et al. | 564/409 |
| 3,862,233 | 1/1975 | Dunn | 564/409 |
| 4,128,582 | 12/1978 | Governale et al. | 564/409 |
| 4,760,185 | 6/1988 | Becker | 564/409 |

*Primary Examiner*—Glennon H. Hollrah
*Assistant Examiner*—Scott C. Rand
*Attorney, Agent, or Firm*—Sprung Horn Kramer & Woods

[57] ABSTRACT

Alkylated aromatic amines can be isolated from crude catalyst-containing mixtures of these with olefins by a procedure in which in general equivalent amounts of an inorganic base and water are added to the alkylation mixture, the catalyst is hydrolysed, the water present in the reaction mixture after the hydrolysis is removed by distillation and the solid catalyst residue is separated off. The catalyst-free alkylation mixture which remains is then fed to customary further working up.

20 Claims, No Drawings

PROCESS FOR THE ISOLATION OF ALKYLATED AROMATIC AMINES

BACKGROUND OF THE INVENTION

The invention relates to a process for the isolation of alkylated aromatic amines by working up crude catalyst-containing alkylation mixtures of such amines from alkylation with the aid of olefins.

Alkylation of aromatic amines and diamines with olefins in the presence of catalytic amounts of aluminum/aluminum chloride is known (Angew. Chemie 69 (1957), 124–131). This reaction has been extended by the use of aluminum/zinc/aluminum chloride (European Pat. No. 0,150,770). Carrying out this reaction in the presence only of $AlCl_3$ is furthermore known (European Pat. No. 0,260,251).

After the alkylation reaction, the crude alkylation mixtures are worked up in a known manner by extraction by stirring with excess dilute aqueous sodium hydroxide solution. The contact catalyst dissolved in the organic phase is in this way decomposed and transferred to the aqueous-alkaline layer. The crude alkylated amine can be isolated by separation of the layers and fed to further working up, for example by distillation.

This known working up process has disadvantages, in particular for ecological reasons: because of the industrial importance of this amine alkylation, it is carried out on a large scale, so that large amounts of waste sodium hydroxide solution are obtained as a byproduct. The waste sodium hydroxide solution contains amine impurities which, as a result of poor separation of the layers, are present in emulsified form. It is not possible to dispose of this contaminated waste sodium hydroxide solution without an expensive purification process.

SUMMARY OF THE INVENTION

A process has now been found for the isolation of alkylated aromatic amines by working up crude mixtures from the alkylation of aromatic amines with olefins containing metal and/or metal halide catalyst, which is characterized in that an inorganic base in an amount which is at least equivalent to the amount of the catalyst halide and water in an amount which is at least sufficient to hydrolyse all the catalyst metal are added to the alkylation mixture, the water present in the reaction mixture after the hydrolysis is then removed by distillation, the solid catalyst residue is separated off and the catalyst-free alkylation mixture which remains is fed to a customary further working up.

DETAILED DESCRIPTION OF THE INVENTION

Aromatic amines which are to be employed for the alkylation are those of the formula

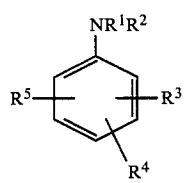
(I)

in which $R^1$ and $R^2$ independently of one another denote hydrogen, methyl or phenyl which is substituted by $R^3$, $R^4$ and $R^5$, $R^3$ and $R^4$ independently of one another denote hydrogen, straight-chain or branched $C_1$–$C_{10}$-alkyl, straight-chain or branched $C_1$–$C_{10}$-alkoxy, phenyl, fluorine, chlorine or bromine and $R^5$ represents hydrogen, methyl, ethyl or amino.

Aromatic amines of the formula

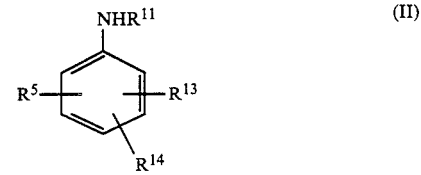
(II)

in which $R^{11}$ denotes hydrogen or phenyl which is substituted by $R^5$, $R^{13}$ and $R^{14}$, $R^{13}$ and $R^{14}$ independently of one another denote hydrogen, straight-chain or branched $C_1$–$C_4$-alkyl, straight-chain or branched $C_1$–$C_4$-alkoxy, phenyl, fluorine or chlorine and $R^5$ represents hydrogen, methyl, ethyl or amino, are preferably employed for the alkylation.

Aromatic amines of the formula

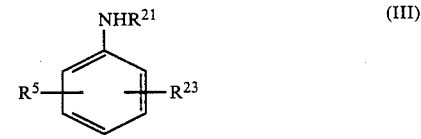
(III)

in which $R^{21}$ denotes hydrogen or phenyl which is substituted by $R^5$ and $R^{23}$, $R^5$ represents hydrogen, methyl, ethyl or amino and $R^{23}$ represents hydrogen, straight-chain or branched $C_1$–$C_4$-alkyl, straight-chain or branched $C_1$–$C_4$-alkoxy or phenyl, are particularly preferably employed for the alkylation.

Important examples of the aromatic amines which can be employed in the alkylation are contained in the following list, which is in no way exhaustive: aniline, o-, m- and p-toluidine, the isomeric xylidenes, o-, m- and p-ethylaniline, o-, m- and p-isopropylaniline, diphenylamine, m-phenylenediamine, toluylene-2,4-diamine, toluylene-2,6-diamine, 1-isopropyl-phenylene-2,4-diamine, 1-isopropyl-phenylene-2,6-diamine, 1-ethyl-phenylene-2,4-diamine, 1-ethyl-phenylene-2,6-diamine and others. Such amines can of course also be employed as a mixture of several of them for the alkylation and then fed to the isolation according to the invention.

The alkenes which can be employed in the alkylation have 2–10 C atoms, preferably 2–6 C atoms and particularly preferably 2–4 C atoms and can be straight-chain or branched. Their double bond can be terminal or internal, preferably terminal. Examples are: ethylene, propylene, but-1-ene, but-2-ene, i-butene and the isomeric amylenes, hexenes, octenes, nonenes or decenes.

Catalysts which are employed for the alkylation are those metal-containing and/or metal halide-containing catalysts which are known to the expert for Friedel-Crafts alkylation. Aluminum-containing catalysts may be mentioned in particular. The aluminum -containing catalysts can contain other metals, such as zinc. Examples are aluminum metal by itself, aluminum metal-/AlCl$_3$, aluminum metal/zinc metal/AlCl$_3$ and AlCl$_3$ by itself.

In such an alkylation, which is not itself the subject of the present invention, the aromatic amines mentioned are mono- or polyalkylated in the nucleus. If the substituents on the N atom or on the nucleus of such aromatic amines denote phenyl, this phenyl substituent can also be mono- or polyalkylated. The nature and scope of such alkylation is unimportant in the context of the present invention. Rather, the fact that all the crude alkylates originating from such an alkylation contains the catalyst used, which has to be separated off and disposed of in order to isolate the pure alkylated aromatic amines, is of importance for the invention and the starting point thereof.

Inorganic bases which can be employed for the process according to the invention are the hydrides, oxides, hydroxides, carbonates, bicarbonates or alkaline salts of other weak acids of the alkali metals and alkaline earth metals. Examples of other weak acids are boric acid, acetic acid and others. The hydroxides, oxides or carbonates of the alkali metals or alkaline earth metals are preferably employed, particularly preferably sodium hydroxide, potassium hydroxide, calcium hydroxide (slaked lime), sodium carbonate, calcium carbonate or calcium oxide (quicklime), especially preferably sodium hydroxide, calcium hydroxide or sodium carbonate.

The amount of inorganic base to be employed for the process according to the invention can vary within wide limits. In principle, it is in a stoichiometric relationship to the catalyst employed. For example, it is possible to employ the base in an amount such that the metal content and the halogen content of the catalyst react completely to give the corresponding salts resulting from the inorganic base. In a particular form, however, it is also possible to employ considerably less base, and in particular in a minimum amount such that the inorganic base to be employed is based stoichiometrically on the halogen content of the catalyst. This has the advantage that a smaller quantity of waste salt is obtained. The amount of inorganic base to be employed thus ranges from the stoichiometric amounts based on the halogen content of the catalyst up to an upper limit, which is to be maintained for economic reasons, of 300%, preferably 150% of the stoichiometric amount of this inorganic base based on the metal content and the halogen content of the catalyst.

The amount of water to be employed for the process according to the invention must be at least sufficient to hydrolyse all the catalyst metal. If alkali metal or alkaline earth metal hydroxides are employed as the inorganic base, this minimum amount of water to be employed can also be the water of reaction inherent in the hydroxides, which leads to the hydroxides of the catalyst metals. For reasons of better reaction of the catalyst constituents with the inorganic base, however, it is advantageous to employ an excess. This is in general 1.1 to 10 times the theoretically required amount, preferably 1.5 to 4 times. This hydrolysis water can be employed according to the invention in the form of the solution or suspension water of the inorganic base. However, it is also possible to employ the water and inorganic base separately in any desired sequence.

The excess water recovered by distillation in the process according to the invention can advantageously be employed as part of the hydrolysis water of a subsequent batch. The process according to the invention in this way operates ideally completely without effluent.

In another advantageous variant, the excess water is removed by azeotropic distillation. Agents which form azeotropes with water are known to the expert; examples which may be mentioned are: aromatic hydrocarbons, such as benzene, toluene or xylene, (cyclo)aliphatic hydrocarbons, such as isooctane, decane, isododecane, cyclohexane and methylcyclohexane, and others. Excess alkene originating from the alkylation can even be used as an agent which forms an azeotrope if it has a suitable boiling situation; examples of these are diisobutylene and tripropylene. All the agents which form azeotropes are employed or recycled from a water separator in an amount such that all the excess water can be distilled azeotropically; any alkene present from the alkylation which is used as an agent which forms an azeotrope likewise falls under this definition of the amount.

The process according to the invention is carried out at 30°–150° C., preferably at 50°–140° C. This temperature is largely not critical. The decomposition of the catalyst which takes place at this temperature is followed by distillation of the excess water, in the course of which decomposition of the catalyst is brought to completion. The temperature which establishes itself during the distillation of the water depends on the substrate and furthermore on the decrease in concentration of the water; the distillation can be carried out under normal pressure or under reduced pressure, that is to say in the range from 400 to 1000 mbar. Such distillations are familiar to the expert.

In the process according to the invention, the inorganic base and water, preferably in the form of an aqueous solution or suspension of the inorganic base, are added to the catalyst-containing alkylation mixture, with thorough stirring. During this procedure, the temperature rises because of the exothermic reaction of the decomposition of the catalyst (hydrolysis and salt formation, as described above). When this exothermic reaction has subsided, the mixture is heated further, whereupon the decomposed catalyst precipitates. In the preferred distillation under normal pressure, the distillation of the water of solution and reaction starts from a bottom temperature of 100° C. This distillation of the water is continued up to a bottom temperature of 140°–160° C. After removal of the water, the decomposed catalyst is present in the alkylation mixture as a dry granular salt. This waste salt can be removed in a known manner by filtration, centrifugation or decanting. Such removal, for example by filtration, can be carried out at room temperature; however, it is more advantageously carried out at an increased temperature of, for example, 30° to 60° C. The filtrate is free from salts and catalyst residues and free from water and can be fed directly to customary further working up, for example fine distillation.

Waste salt (catalyst residue) removed can be freed from small amounts of the alkylation mixture by washing with an organic solvent. The organic solvent used for this depends in a manner which is known to the expert on the solubility of the alkylated amines and can be, for example, an aromatic, aliphatic or cycloaliphatic hydrocarbon, for example benzene, toluene, xylene, isooctane, benzine fractions or cyclohexane. After removal of the washing agent by drying or dry blowing, the washed waste salt can be fed to a dump for disposal.

It goes without saying that the amine-containing washed solution and the solvents released during drying or dry blowing are recovered and fed to suitable circulations.

EXAMPLE 1

39 g of 20 % strength sodium hydroxide solution were added dropwise, while stirring, to the catalyst-containing crude alkylate of an ethylation of 250 g of a mixture of toluylene-2,4-diamine and toluylene-2,6-diamine in a ratio of 65:35 with 8.33 g of aluminum chloride and 4.72 g of aluminum/zinc 90:10 and ethylene to give a mixture of 6-methyl-2,4-diethylphenylene-1,3-diamine and 2-methyl-4,6-diethylphenylene-1,3-diamine at 40°–50° . Thereafter, the temperature rose to 80°–90° C. A yellowish salt precipitated. The temperature was increased slowly to 140° C. and 21.8 g of water were distilled off. The salt-containing alkylate was filtered off with suction between 90° and 120° C. The yellowish salt remained on the suction filter. Still adhering alkylate could be dissolved out by washing this salt twice with 25 ml of toluene each time. The salt obtained in this manner weighed 23.7 g when dry.

EXAMPLE 2

10.4 g of sodium carbonate and 32 g of water were added to the contact catalyst-containing crude alkylate of an ethylation of 250 g of toluylene-2,4-diamine with 8.33 g of aluminum chloride and 4.72 g of aluminum/zinc 90:10 and ethylene to give 6-methyl-2,4-diethylphenylene-1,3-diamine at 30°–40° C. and the procedure was as described in Example 1. 24.2 g of waste salt were obtained.

EXAMPLE 3

45 ml of water and 7 g of calcium oxide were added to the contact catalyst-containing crude alkylate of an ethylation of 290 g of p-toluidine with 10.8 g of aluminum chloride and 5.4 g of aluminum and ethylene to give 4-methyl-2,6-diethyl-aniline at 40°–50° C. and the procedure was as described in Example 1. 29 g of waste salt were obtained.

EXAMPLE 4

185 g of 20 % strength sodium hydroxide solution were added dropwise to the contact catalyst-containing crude alkylate of a propylation of 240 g of aniline in the presence of 40 g of aluminum chloride and 4 g of aluminum and propylene to give 2,6-diisopropyl-aniline at 40° to 50° C. and the procedure was as described in Example 1. 96 g of waste salt were obtained.

EXAMPLE 5

The catalyst-containing crude alkylate of a reaction of 126.7 g of diphenylamine with 266 g of diisobutylene in the presence of 5 g of aluminum chloride to give 4,4′-di(α,α,γ,γ-tetramethylbutyl)-diphenylamine was stirred with 13.3 g of 45% strength sodium hydroxide solution in an autoclave at 135° C. for 2 hours. The water was then removed by azeotropic distillation with the aid of the excess diisobutylene. 4.5 ml of water were in this way obtained. After the filtration, 10.4 g of waste salt were obtained.

What is claimed is:

1. In a process for the isolation of alkylated aromatic amines comprising working up crude mixtures from the alkylation of aromatic amines with olefins containing metal catalysts and/or metal halide catalysts, wherein when a metal halide catalyst is employed an inorganic base in an amount which is at least equivalent to the amount of the catalyst halide is added to the alkylation mixture, and wherein water in an amount which is at least sufficient to hydrolyze all the catalyst metal is added to the alkylation mixture, the improvement which comprises removing by distillation the water present in the reaction mixture after the hydrolysis, separating off a solid catalyst residue and feeding a catalyst-free alkylation mixture which remains to the working up.

2. The process according to claim 1, wherein aromatic amines of the formula

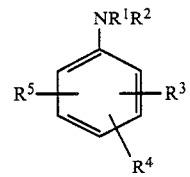

in which
R$^1$ and R$^2$ independently of one another denote hydrogen, methyl or phenyl which is substituted by R$^3$, R$^4$ and R$^5$,
R$^3$ and R$^4$ independently of one another denote hydrogen, straight-chain or branched C$_1$–C$_{10}$-alkyl, straight chain or branched C$_1$–C$_{10}$-alkoxy, phenyl, fluorine, chlorine or bromine and
R$^5$ represents hydrogen, methyl, ethyl or amino, are employed for the alkylation.

3. The process according to claim 2, wherein aromatic amines of the formula

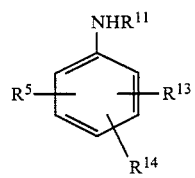

in which
R$^{11}$ denotes hydrogen or phenyl which is substituted by R$^5$, R$^{13}$ and R$^{14}$,
R$^{13}$ and R$^{14}$ independently of one another denote hydrogen, straight-chain or branched C$_1$–C$_4$-alkyl, straight-chain or branched C$_1$–C$_4$-alkoxy, phenyl, fluorine or chlorine and
R$^5$ represents hydrogen, methyl, ethyl or amino, are employed for the alkylation.

4. The process according to claim 3, wherein aromatic amines of the formula

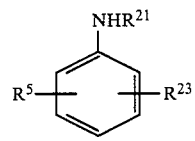

in which
R$^{21}$ denotes hydrogen or phenyl which is substituted by R$^5$ and R$^{23}$,
R$^5$ represents hydrogen, methyl, ethyl or amino and $R^{23}$ represents hydrogen, straight-chain or branched $C_1$-$C_4$-alkyl, straight-chain or branched $C_1$-$C_4$-alkoxy or phenyl are employed for the alkylation.

5. The process according to claim 1, wherein straight-chain or branched $C_2$-$C_{10}$-olefins are employed.

6. The process according to claim 5, wherein straight-chain or branched $C_2$-$C_6$-olefins are employed.

7. The process according to claim 6, wherein straight-chain or branched $C_2$-$C_4$-olefins are employed.

8. The process according to claim 1, wherein an aluminum-containing catalyst is present in the crude alkylation mixture.

9. The process according to claim 8, wherein Al, Al/AlCl$_3$, Al/Zn/AlCl$_3$ or AlCl$_3$ is present in the crude alkylation mixture.

10. The process according to claim 1, wherein the hydrides, oxides, hydroxides, carbonates, bicarbonates or alkaline salts of other weak acids of the alkali metals and alkaline earth metals are employed as the inorganic bases.

11. The process according to claim 1, wherein the inorganic base is employed in an amount which extends from the amount based stoichiometrically on the halogen content of the catalyst up to 300% of the amount based stoichiometrically on the metal content and the halogen content of the catalyst.

12. The process according to claim 11, wherein the inorganic base is employed up to 150% of the amount based stoichiometrically on the metal content and the halogen content of the catalyst.

13. The process according to claim 1, wherein the water is added in an amount which is 1.1 to 10 times the amount sufficient for hydrolysis of the catalyst metal.

14. The process according to claim 13, wherein the water is added in an amount which is 1.5 to 4 times the amount sufficient for hydrolysis of the catalyst metal.

15. The process according to claim 1, wherein the excess water is removed by distillation under 400 to 1000 mbar up to a bottom temperature of 140°-160° C.

16. The process according to claim 15 wherein the excess water is removed by distillation under normal pressure.

17. The process according to claim 1, wherein an agent which forms an azeotrope is added for removal of the excess water by distillation.

18. The process according to claim 1, wherein the water which remains after the hydrolysis and has been removed by distillation is employed as part of the hydrolysis water of a subsequent batch.

19. A process according to claim 1, wherein the further working up comprises a distillation.

20. A process according to claim 1, wherein the further working up comprises a fine distillation.

* * * * *